United States Patent [19]

Densert et al.

[11] Patent Number: 4,757,807

[45] Date of Patent: Jul. 19, 1988

[54] METHOD AND APPARATUS FOR TREATING MENIERE'S DISEASE

[76] Inventors: Barbara Densert; Ove Densert, both of Broddesonsgatan 22, S-302 34 Halmstad, Sweden

[21] Appl. No.: 1,795

[22] Filed: Jan. 9, 1987

[30] Foreign Application Priority Data

Nov. 7, 1986 [EP] European Pat. Off. ........ 86850390.5

[51] Int. Cl.⁴ .................... A61H 23/00; A61B 5/12; A61B 5/03
[52] U.S. Cl. ........................ 128/40; 128/64; 128/746; 128/38
[58] Field of Search .............. 128/40, 39, 38, 32, 128/64, 54, 44, 24 R, 746, 747

[56] References Cited

U.S. PATENT DOCUMENTS

| | | | |
|---|---|---|---|
| 841,146 | 1/1907 | Hasbrouck | 128/40 |
| 976,200 | 11/1910 | Meyer | 128/39 |
| 1,678,564 | 7/1928 | Eldred | 128/38 |
| 1,678,565 | 7/1928 | Eldred | 128/38 |
| 2,014,009 | 9/1935 | Vance | 128/40 |
| 2,264,422 | 12/1941 | Wells | 128/40 |
| 2,626,601 | 1/1953 | Riley | 128/40 |
| 2,652,048 | 9/1953 | Joers | 128/40 |
| 4,021,611 | 5/1977 | Tomatis | 73/585 |
| 4,184,510 | 1/1980 | Murry et al. | 128/305 |

FOREIGN PATENT DOCUMENTS

WO83/02556  8/1983  PCT Int'l Appl. .
10695  of 1908  United Kingdom .
23385  of 1911  United Kingdom ............ 128/39

Primary Examiner—Edgar S. Burr
Assistant Examiner—Tonya Lamb
Attorney, Agent, or Firm—Armstrong, Nikaido, Marmelstein & Kubovcik

[57] ABSTRACT

In a method and apparatus for the generation and transmission of complex pressure surges to the fluid system of the inner ear, this fluid system comprising an outer fluid chamber (perilymphatic space) provided with inlet and outlet, which entirely surrounds an inner fluid chamber (endolymphatic space), the fluid volume therein regulating the hearing ability of the ear in order, through intermittent compression of said inner chamber, to reduce any impairment of the hearing which may exist due to expansion of said chamber caused by too large a volume of fluid in said inner chamber, reproducible pressure pulses or surges are produced, consisting of a first pressure component (a) having varying pressure oscillations, and a second component (b) superimposed on said first component (a) and having a predeterminable overpressure, said first component (a), by means of rapidly repeated pressure variations, substantially blocking the passage of fluid from the outer fluid chamber, in addition to which the said component (b) via the original volume of fluid thus retained in the outer chamber, intermittently compresses the inner fluid chamber in order to regulate the fluid volume therein.

11 Claims, 2 Drawing Sheets

METHOD AND APPARATUS FOR TREATING MENIERE'S DISEASE

BACKGROUND OF THE INVENTION

Field of the Invention

The present invention relates to a method and apparatus for the generation and transmission of predeterminable complex pressure surges to the fluid system of the inner ear, in order to achieve intermittent compression of the fluid system in the labyrinth of the inner ear.

More specifically the invention relates to a method and apparatus for the generation and transmission of complex pressure surges to the fluid system of the inner ear, this fluid system comprising an outer fluid chamber (perilymphatic space) provided with inlet and outlet, which entirely surrounds an inner fluid chamber (endolymphatic space), the fluid volume therein regulating the hearing ability of the ear in order, through intermittent compression of said inner chamber, to reduce any impairment of the hearing which may exist due to expansion of said chamber caused by too large a volume of fluid in said inner chamber.

The apparatus provided according to the invention can be used with advantage to influence the relation between the two fluid systems of the inner ear (perilymphatic and endolymphatic) when the membranous labyrinth is swollen (Meniere's disease).

The invention can also be used to study the effects of various types of pressure waves, for instance, infrasound on the function of the inner ear in animals and humans.

It has been established that alterations in the endolymphatic space affect the functioning of the ear and that certain diseases are attributable to such alterations. Examples are Meniere's disease, characterised by symptoms such as loss of hearing, dizziness, tinnitus, feelings of the ear being blocked, etc. This often results in complete inability to work, partially due to impaired functioning of the ear but primarily because of the psychological effect which in some cases may be drastic. Surgical treatment of the endolymphatic sac has been attempted but the results have either been short-lived or non-existent.

In 1908 British Pat. No. 10,695 proposed a vibratory apparatus for treating pathological states in the tympanic membrane to relieve "head noise" and other undefined forms of impaired hearing. According to the description of this British Patent, both positive and negative pressure are used which, as is clear from the following description of the invention, cannot solve the present problem.

There has also recently been discussion of influencing the hydrodynamic systems of the inner ear by applying a pressure alteration in the auditory meatus. The device utilised comprised first means for generating a static pressure level, second means for varying the static pressure level, and third means for connecting the first and second means to the auditory canal. Although this proposal touches upon the idea of influencing the hydrodynamic system inside the ear, it offers no practical solution of the existing problem since the necessary build-up of special complex pulses, which is proposed according to the present invention, cannot be inferred from this publication.

SUMMARY OF THE INVENTION

It has now surprisingly been found possible to eliminate the drawbacks of such proposals and the present invention therefore provides an apparatus for applying reproducible pressure pulses or surges to the fluid system of the ear, the pressure pulses or surges consisting of a first pressure component (a) having varying pressure oscillations, and the second component (b) superimposed on said first component (a) and having a predeterminable overpressure, said first component (a), by means of rapidly repeated pressure variations, substantially blocking the passage of fluid from the outer fluid chamber, in addition to which the component (b) via the original volume of fluid thus retained in the outer chamber, intermittently compresses the inner fluid chamber in order to regulate the fluid volume therein.

Other characteristic features of the invention are revealed in the accompanying claims.

The invention is based on the observation that the peripheral hearing and balance function are localised in the inner ear which consists of a bone casing enclosing membranes and receptors forming the perilymphatic and endolymphatic spaces which are filled with fluid. The inner ear fluids transport sound energy through the inner ear, thus functionally coordinating the various structures of the inner ear. The relative volume and chemical composition of these fluids are of decisive significance to the function of the inner ear. An increase in the volume of fluid in the membranous labyrinth (endolymphatic space) is believed to produce symptoms such as impaired hearing, dizziness and a feeling of pressure in the ear (Meniere's disease). It is believed that the level of these afflictions can be directly related to an increase in this fluid volume.

The hydrodynamic system of the inner ear is equipped with a number of pressure-regulating mechanisms which permit the inner ear to function normally under physiological pressure variation. The pressure-equalising ability of the inner ear allows re-distribution of the fluid in the inner ear and the intravascular fluids via pressure-equalisation canals in the event of, for instance, changes in the position of the body or in the blood pressure and during coughing. Experiments on animals have provided knowledge of the capacity of these canals and it has been possible to discover the conditions necessary to cause the flow of fluid through them. It has been found that, with the aid of complex pressure pulses produced by means of the invention, it is possible to force more fluid through certain of these canals than through others.

This differentiated fluid flow is made possible by existing differences between the various canals, i.e. their pressure-regulating capacity, and the fact that within the rigid walls of the bony labyrinth the total volume of fluid must remain the same. Since the perilymphatic and endolymphatic spaces are anatomically entirely separate, and each is equipped with its own pressure-equalising canals, i.e. paths of flow, it should be possible to reduce the endolymph without at the same time noticeably affecting the volume of perilymph this being achieved by application of the complex pressure pulses according to the invention. The effect achieved by the invention indicates that this is indeed the case at least with Meniere's disease since the increased endolymph volume is believed to be directly proportional to the degree of dysfunction of the inner ear. In order to achieve the effect aimed at by the invention, i.e. insofar as possible to induce fluid to flow out through the endolymphatic canals, the main canal for perilymphatic flow, the cochlear aqueduct, should be incapacitated.

Clinical tests using the method according to the invention have shown that the fluid flow varies in individual canals dependent on their anatomic shape and functional capacity and it should therefore be possible to vary the pressure pulses in such a way as to impede flow through the aqueduct while a general pressure increase simultaneously stimulates the flow through other outflow paths. It has thus been found according to the invention that a sine wave superimposed on the basic pressure is able to produce a turbulent flow through the aqueduct, thus inducing partial functional blockage thereof. Due to the individual differences in anatomy of the aqueduct described above, this blockage is time related (i.e. the flow through the aqueduct can be described in time constants). The duration of the pressure pulses and the interval between successive pulses are thus of great significance and should be individually adjusted. It must be possible to vary the frequency of the sine wave since, due to resonance phenomena, it is presumed that certain frequencies are more efficient than others. According to the invention, therefore, it is possible to adjust the total amplitude of the pressure variations to levels inducing maximum re-distribution of fluid between the inner and outer labyrinths.

While the supply of a positive pressure pulse may stimulate outflow of the endolymph and reduce endolymphatic swelling, the reverse, i.e, supply of a negative pressure pulse, may induce increased supply of endolymph, followed by deterioration and increased irritation. A system for the supply of a complex pressure pulse according to the invention should therefore suitably be provided with a safety device preventing negative pulses.

Since no direct method exists in practice for measuring the fluid pressure in the inner ear of living human beings, an indirect measurement of the hydrodynamic balance should be used when the inner ear is subjected to pressure pulses generated according to the invention. A clinical-audiological evaluation method entailing observation of the patient's subjective symptoms such as dizziness and a feeling of pressure in the ear, as well as measurement of the hearing function, has been proposed. The hearing function is evaluated with the aid of classical test batteries as well as methods specifically designed for measuring audiological signal analysis. The latter method can also be used for measuring psycho-acoustic tuning curves (PTC) and is considered capable of quantitatively describing the degree of disturbance affecting the signal-analytical part of the inner ear. This functional disturbance can be related to the degree of swelling within the membranous labyrinth in the case of Meniere's disease.

The model described above for evaluating the function of the inner ear in conjunction with exposure to pressure pulses is indispensible as a step in the selection of adequate pressure parameters and must therefore be included as an important part of the treatment.

BRIEF DESCRIPTION OF THE DRAWINGS

The invention will be described more fully in the following, with reference to the accompanying drawings, in which.

DETAILED DESCRIPTION OF THE INVENTION

Figure 1:
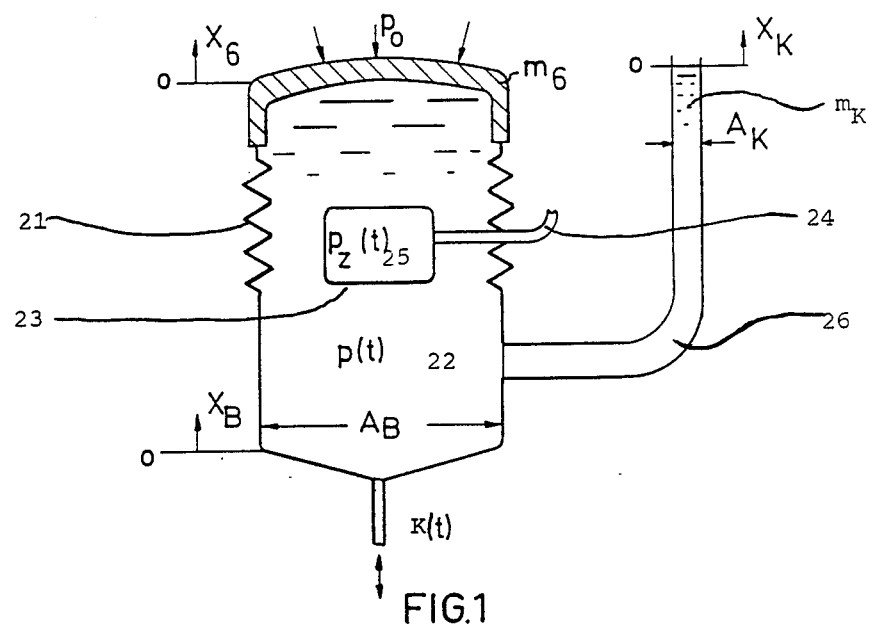
FIG. 1 is a mathematical model illustrating the principle applied according with the invention.

The process actually occurring during the application of complex pressure pulses according to the invention is not fully understood but probably entails the principles described below with reference to the mathematical model shown in FIG. 1.

In principle and as shown in the model, the inner ear comprises a fluid labyrinth consisting of a casing of a semipermeable membrane 21 which is filled with tissue fluid 22. An inner system 23 floats in, or is entirely surrounded by an outer system comprising fluid 22 and communicates with the exterior through membranes or canals represented by conduit 24. The inner system is filled with fluid 25. The membrane 21 of the outer system is suspended in the body (not shown) and also has an outlet canal 26.

In principle a periodic force K (t) is produced on the outer system by means of the invention, through a suitable pressure-wave generator, this force increasing the fluid pressure in the outer system within the limits of elasticity, in the form of pump strokes. The tissue mass $m_6$ of the outer system will thus be displaced, causing the constricted tissue mass to seek sufficient space elsewhere and the tissue fluid will therefore usually flow into canal 26($A_k$). The outer casing 21 is characterised here with respect to elasticity by the constant C. If it is now assumed that the lower surface $A_B$ moves periodically in the vertical direction, the outer casing 21 is influenced by this at low frequencies to an extent corresponding to $X_6$ and the fluid column in the canal 26 is correspondingly displaced by $X_K$. The bottom fluid, with surface $A_B$, is displaced by $X_B$ towards the top of the model, see $A_B$, $X_6$ and $A_K$, $X_K$, respectively.

Without considering the inner system, the harmonious movement of the three following systems can be observed (1) An initiating force K (t) will move up and down the special outer spot of the casing (t denotes time)

(2) The outer system, mass $m_6$ will be sychronously compressed or expanded.

(3) The canal tissue column with mass $m_k$ will synchronously oscillate.

According to the invention, a pressure function p (t) is initiated within the outer system in such a way that fluid flow via the outer canal is prevented, whilst at the same time a strong pressure surge is applied to the inner system, overcoming the flow resistance in the outflow paths of the inner system and achieving a small release of the tissue fluid.

1. The outer system

The system proposed enables valid differential equations to be established for the movement of the tissue mass $m_6$ and for the movement of the canal column $m_K$. If the following harmonic functions are established for the oscillation generated through the oscillation reactor according to the invention $$X_B = A^* \sin \omega t + g(t) \qquad (1)$$

in which $\omega$ denotes the generation frequency, the following differential equation is obtained for the tissue mass $$\ddot{X}_6 + \frac{c}{m_6} \cdot X_6 = \frac{A_B}{m_6}[p(t) - p_o] \quad (2)$$

The damping effect has been disregarded here, and simplified fringe conditions have been selected. In similar manner the following is obtained for the canal mass $m_K$ $$\ddot{X}_K = \frac{A_K}{m_K}[p(t) - p_o] \quad (3)$$

Since continuity equations also give $$A_B \cdot X_B = A_B X_6 + A_K \cdot X_K \quad (4)$$

and after a certain amount of conversion and specific transformations, the following differential equation is obtained for the canal mass $$\ddot{X}_K \beta \ddot{X}_K = \alpha X_B \delta X_B \quad (5)$$

This means that $$\beta = f \cdot \alpha \cdot \frac{c}{m_6} \text{ and } \sigma = \alpha \cdot \frac{c}{m_6} \quad (6) \text{ and } (7)$$

with $$\alpha = \frac{f}{f^2 + \mu}, f = \frac{A_K}{A_B} \text{ and } \mu = \frac{m_K}{m_6} \quad (8), (9) (10)$$

c denotes the resilience constant of the resilient outer casing. In equation (1) A* is the amplitude of the harmonic oscillation conversion of the outer membrane and g (t) is an additional function which can subsequently be identified as a pressure surge of limited duration. If the surge function g (t) is disregarded initially, the homogeneous differential equation of equation (5) can be solved and the following is obtained $$X_{K,H} = a \cdot \sin[\sqrt{\beta \cdot t}] \quad (11)$$

whereupon, with the given fringe conditions for the amplitude, $$a = A^* \frac{\omega/\omega_E}{1 - (\omega/\omega_E)^2} \left[ \frac{1}{f} - \alpha \cdot \left(\frac{\omega}{\omega_E}\right)^2 \right] \quad (12)$$

can be derived. The natural frequency of the system's own tendency to oscillation is identical to $\sqrt{\beta}$ and the following therefore applies:

$$\omega_E = \sqrt{\beta} \quad (13)$$

The ratio of the generation frequency $\omega$ to generation frequency $\omega_E$ is of great significance here, as usual. A specific solution of differential equation (5) can be derived via $$X_{K,I} = B \cdot A^*[-\alpha\omega^2 + \theta]\sin \omega t \quad (14)$$

with $$B = \frac{1}{\beta - \omega^2} \quad (15)$$

and the total solution is therefore $$X_K = a \cdot \sin\omega_E t + \frac{1}{\omega_E^2 - \omega_2} \cdot A^*[-\alpha\omega^2 + \delta]\sin\omega t \quad (16)$$

for the speed of the canal mass $\ddot{X}_K$. For the time-related outflow of the mass the following applies $$\dot{m}_K = \rho \cdot A_K \cdot \dot{X}_K \quad (17)$$

with a tissue fluid density $\rho$. After substitution follows $$\frac{m_K}{\rho A_K \cdot A^* \cdot \omega_E} = \quad (18)$$

$$\frac{\omega/\omega_E}{1 - (\omega/\omega_E)^2} \left[ \frac{1}{f} \alpha - \left(\frac{\omega}{\omega_E}\right)^2 \right] \cos \omega_E t + \cos\omega t$$

thus enabling assertion of the mass flowing into the outlet canal. This flow approaches 0 when $$\frac{1}{f} = \left(\frac{\omega}{\omega_E}\right)^2 \quad (19)$$

At an initiation frequency $\omega$, therefore, the oscillation generator must be set in accordance with the following $$\frac{\omega}{\omega_E} = \sqrt{1 + \left(\frac{A_B}{A_K}\right)^2 \cdot \frac{m_K}{m_6}} \quad (20)$$

Since the outer surface $A_B$ of the tissue is extremely large in relation to the flow in the canal $A_K$, the quadratic influence of this ratio dominates.

The canal mass $m_K$ is admittedly much less than the tissue mass in the outer system. In all the frequency ratio is $\omega/\omega_E > 1$, which logically, and as expected, is overcritical. The oscillation generator must therefore be set at an initiation frequency $\omega$, which lies above the natural frequency.

$$\omega_E = \sqrt{f \cdot \alpha} \cdot \sqrt{\frac{c}{m_6}} \quad (21)$$

It can be assumed that this natural frequency is extremely low since the spring resistance c is probably slight, the tissue fluid $m_6$ in the outer system is relatively large, while the surface ratio f is also small.

Equation (18) for the outflowing canal mass does not yet include the momentary, time-limited surge influence, since the mathematical procedure is extremely complicated.

2. Inner system

A closed solution of the differential equation with the surge function g (t) is extremely complicated and has not therefore been described in detail. The pressure function which can be appraised from equation (3)

$$p(t) - p_o = \frac{\ddot{X}_K \cdot m_K}{A_K} \quad (22)$$

will govern the absolute pressures in the outer tissue fluid in accordance with the amplitudes set in the oscillation generator. A peak pressure could be briefly generated by means of the superimposed pressure surge which, through its influence on the central system, could effect the desired flow of fluid. Obviously the pressure surge used here would have to be optimized. When the canal mass flows back, the pressure surge is applied to the inner chamber, thus compressing it. The backwardly flowing mass would only cause increased stretching of the tissue membrane in the outer system. The outlet remains blocked and, due to the surge, a rapid dampening of the stable harmonic oscillation state is achieved.

Figure 2:
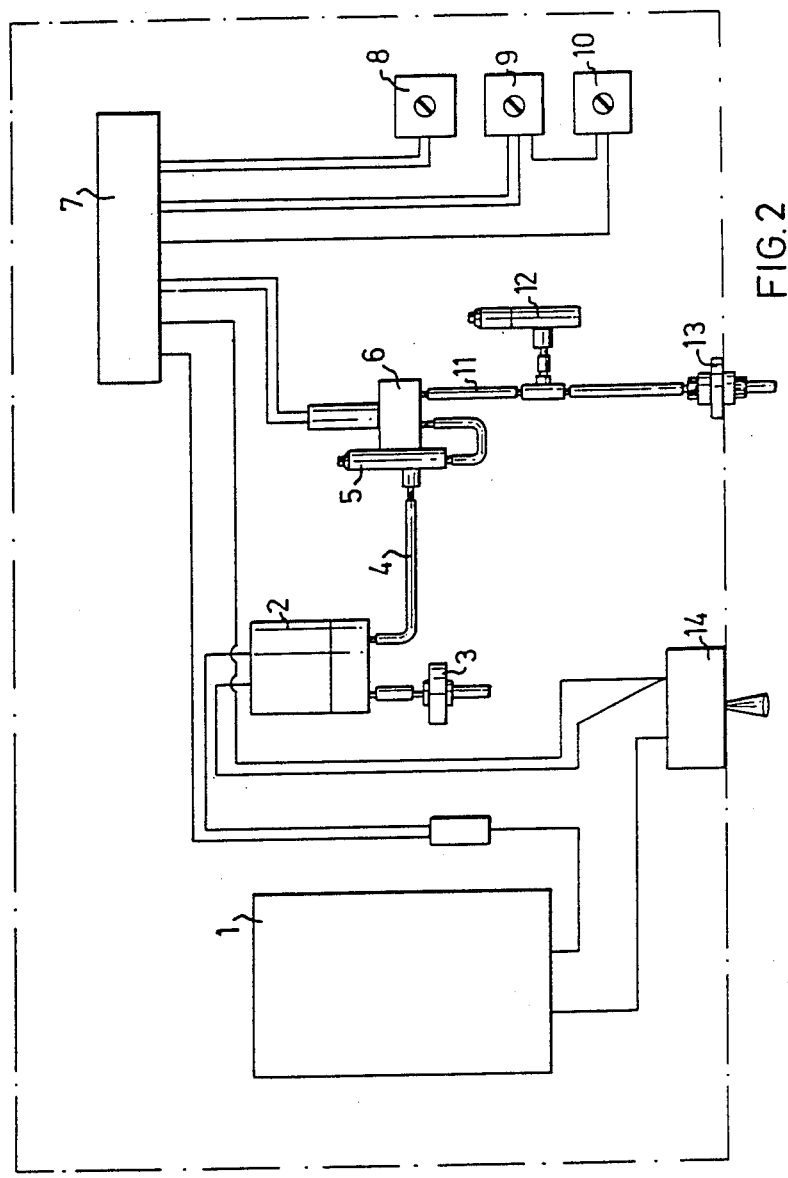
FIG. 2 is a diagrammatic view of an apparatus constructed in accordance with the invention.

FIG. 2 shows a diagrammatic sketch of an apparatus in accordance with the invention in which 1 denotes a current source—suitably consisting of a number of batteries. 2 denotes a pressure-generating means such as a membrane pump or rotary pump. A silencer 3 is advisable if a rotary pump is used. The pressure generated in the pump is conducted via pipe 4 and a non-return valve 5 serving as throttle, to a three-way valve 6. The frequency and durations of the pressure surges are governed by a number of electronic circuits 7 via potentiometers 8, 9, 10.

The complex pressure surges thus obtained pass through pipe 11 via a non-return valve 12 serving as leakage valve and via suitable connections 13 to the inner canal of the ear.

Each apparatus is initially set with respect to amplitude, frequency and duration, within a range previously determined by experiment as being suitable, and is subsequently adjusted for each patient before the apparatus is handed over for permanent use.

The apparatus thus consists of an electronic part and a pneumatic part. The electronic part comprises two printed circuit boards. The first board governs the pulse length and interval between pulses, the pulse length and intervals between pulses varying individually from 0 to 20 seconds.

The second printed circuit board governs the pressure modulation and determines frequency and modulation, suitably variable between 1 and 20 Hz. These two printed circuit boards also control an electropneumatic, two-way valve by which the air flow to and from the ear can be varied. The pneumatic part thus consists of said pump, generating the air flow, and said valve.

Alternatively the air flow may be regulated by a speed controller controlling the speed of pump, or by a combination of this and the non-return valve described above.

The non-return valve 12 regulates the total amplitude of the pressure.

The apparatus is equipped with batteries. Of course the current may be supplied directly from a power point if desired. 14 denotes a switch.

The design described permits the use of a frequency spectrum from 3 to 20 Hz.

To investigate whether the effects of these pressure pulses could be considered superior to known technology, some ten patients were treated with the aid of pressure pulses produced according to the invention.

The total amplitude of the pulse was varied from 10 to 30 cm water column and the modulation amplitude was varied from 25 to 0 cm water column. The frequencies varied from 3 to 15 Hz and the pulse length could be varied from 0.5 to 5 seconds. Pulses were initiated every 4.5 seconds and the ear was thus exposed for 5 to 10 minutes, after which treatment was repeated every two hours to start with. Once the clinical effect had been established, treatments were reduced to 3 or 4 per day.

The pressure parameters were varied steplessly. Times and frequency of exposure were varied individually within the limits stated above. Patients with extremely varying degrees of impaired hearing were selected, including those with advanced loss of hearing.

It was found that the clinical improvement normally occurred within a few days or hours of starting the treatment. The improvement covered problems of dizziness, feelings of pressure and audio-function.

Objective measurement of the audio-function showed significant improvement.

Preliminary experience from these tests showed the equipment to be easy to use as well as extremely effective from the therapeutic point of view.

The explanation for this is probably that the pressure set, and thus the technical effect, could be kept constant throughout the treatment. Unstable pressure was thus prevented.

The availability of various frequencies of the pulse modulation facilitates finding the resonance frequency considered optimal for a patient, which varies individually depending on the size and capacity of the equalization canals in the inner ear.

The design according to the invention offers excellent opportunity for varying the parameters of the pressure pulse. The optimal combination of parameters specific to an individual can be determined, tested and guaranteed for the patient.

The difference between clinical improvement, no improvement or even deterioration of the condition lies in finding an optimal combination of all pressure parameters for each patient, which can effect a flow of endolymph through the endolymphatic canal from the membranous labyrinth, while simultaneously blocking the flow through the cochlear aqueduct. Through a series of experiments carried out on animals, the point for functional blockage was found to be extremely sensitive, i.e. dependent on very slight variations in the pressure parameters.

The invention is of course not limited to the apparatus shown in FIG. 2 but can be varied in many ways within the scope of the following claims.

We claim:

1. Apparatus for the generation and transmission of complex pressure surges to the fluid system of the inner ear, this fluid system comprising an outer fluid chamber (perilymphatic space) provided with inlet and outlet, entirely surrounding an inner fluid chamber (endolymphatic space), the fluid volume in the outer fluid chamber regulating the hearing ability of the ear in order, through intermittent compression of said inner chamber, to reduce any impairment of the hearing which may exist due to expansion of said inner chamber caused by too large a volume of fluid in said inner chamber, comprising pressure generating means and pressure regulating means for controlled generation and emission of reproducible pressure, said surges consisting of a first pressure component having varying pressure oscillations, and a second pressure component superimposed on said first component and having a predeterminable overpressure; wherein said first component, by means of rapidly repeated pressure variations, substantially blocks the passage of fluid from the outer fluid chamber and wherein the second component, via the original volume of fluid thus retained in the outer chamber, intermittently compresses the inner fluid chamber in order to regulate the fluid volume therein.

2. Apparatus according to claim 1, wherein the regulating means are arranged to emit said second component after a peak effect has been reached in the first component.

3. Apparatus according to claim 1, wherein means are provided to vary the total amplitude of the pressure oscillations between 10 and 30 cm water column.

4. Apparatus according to any one of claims 1 to 3 wherein means are arranged to vary the modulation amplitude from 25 to 0 cm water column.

5. Apparatus according to claim 1, wherein means are arranged to produce frequency variations of between 3 and 15 Hz.

6. Apparatus according to claim 1, wherein the pressure regulating means are arranged to produce a pulse length variation of between 0.5 and 5 seconds and to initiate the pulses every 1 to 6 seconds.

7. Apparatus according to claim 1, comprising an electronic and a pneumatic part, wherein said electronic part consists of first and second printed circuit boards of which said first printed circuit board is arranged to control the pulse length and the interval between pulses, and the second printed circuit board is arranged to control the pressure modulation and its frequency, and wherein said pneumatic part consists of said pressure generating means and regulating valves connected thereto.

8. Apparatus for the generation and transmission of complex pressure surges to the fluid system of the inner ear, this fluid system comprising an outer fluid chamber (perilymphatic space) provided with inlet and outlet, entirely surrounding an inner fluid chamber (endolymphatic space), the fluid volume in the outer fluid chamber regulating the hearing ability of the ear in order, through intermittent compression of said inner chamber, to reduce any impairment of the hearing which may exist due to expansion of said inner chamber caused by too large a volume of fluid in said inner chamber, comprising pressure generating and regulating means for controlled generation and emission of reproducible pressure, said surges consisting of a first pressure component having varying pressure oscillations, and a second component superimposed on said first component and having a predeterminable overpressure, the sum of said first and second components always being positive; wherein said apparatus is arranged so that (i) a complex of parameters individually set for a specific patient, and comprising the frequency and pressure amplitude of the first component and the pressure amplitude of the second component, can be set to cause said first component, by means of rapidly repeated pressure variations, to substantially block the passage of fluid from the outer fluid chamber, and so that (ii) the second component, via the original volume of fluid thus retained in the outer chamber, intermittently compresses the inner fluid in order to regulate the fluid volume therein.

9. A method for treating Meniere's disease comprising applying a succession of positive pressure surges to the perilymphatic space of the ear of a patient suffering Meniere's disease, each surge consisting of a first pressure component having varying pressure oscillations, and a second component superimposed on said first component and having a predeterminable overpressure, the frequency and amplitude of said first component being selected such that the passage of fluid from the perilymphatic space is substantially blocked and said second component being selected intermittently to compress, via the fluid retained in the perilymphatic space, the endolymphatic space of said patient's ear in order to reduce the fluid volume therein.

10. A method according to claim 9 wherein said first pressure component is applied for sufficient duration to achieve blocking of the outlet from the perilymphatic space before said second pressure component is applied.

11. A method according to claim 9 wherein said first and second pressure components are applied by an apparatus having an electronic and a pneumatic part for the generation and transmission of complex pressure surges.

* * * * *